United States Patent
Ristol Debart et al.

(10) Patent No.: US 6,875,848 B2
(45) Date of Patent: Apr. 5, 2005

(54) PROCESS FOR THE PRODUCTION OF VIRUS-INACTIVATED HUMAN GAMMAGLOBULIN G

(75) Inventors: Pere Ristol Debart, Sabadell (ES); Francisco Rabaneda Gimenez, Barcelona (ES); Ma Teresa Lopez Hernandez, Badalona (ES)

(73) Assignee: Probitas Pharma, S.A., Barcelona (ES)

( * ) Notice: Subject to any disclaimer, the term of this patent is extended or adjusted under 35 U.S.C. 154(b) by 108 days.

(21) Appl. No.: 10/052,324

(22) Filed: Jan. 17, 2002

(65) Prior Publication Data

US 2002/0151688 A1 Oct. 17, 2002

(30) Foreign Application Priority Data

Jan. 17, 2001 (ES) .......................................... 200100101

(51) Int. Cl.$^7$ ....................... A61K 39/395; C07K 16/00
(52) U.S. Cl. .................. 530/390.1; 424/176.1; 424/177.1; 530/390.5; 530/414; 530/416; 530/419; 530/421
(58) Field of Search ........................... 424/176.1, 177.1; 530/390.1, 390.5, 414, 416, 419, 421

(56) References Cited

U.S. PATENT DOCUMENTS

| | | | |
|---|---|---|---|
| 4,164,495 A | | 8/1979 | Hansen |
| 4,374,763 A | * | 2/1983 | Takagi |
| 4,876,088 A | * | 10/1989 | Hirao et al. |
| 5,177,194 A | * | 1/1993 | Sarno et al. |
| 5,234,685 A | | 8/1993 | Eibl et al. |
| 6,124,437 A | * | 9/2000 | Hirao et al. |
| 6,159,471 A | * | 12/2000 | Hirao et al. |
| 6,281,336 B1 | * | 8/2001 | Laursen et al. |
| 6,441,144 B1 | * | 8/2002 | Mamidi et al. |

FOREIGN PATENT DOCUMENTS

| | | |
|---|---|---|
| EP | 0 911 037 A1 | 4/1999 |
| WO | 8400891 * | 3/1984 |
| WO | WO-95/18155 A1 | 7/1995 |
| WO | WO-99/18130 A1 | 4/1999 |
| WO | WO-99/33484 A1 | 7/1999 |
| WO | WO 99/64462 A1 | 12/1999 |

* cited by examiner

*Primary Examiner*—David Saunders
(74) *Attorney, Agent, or Firm*—Darby & Darby

(57) ABSTRACT

The gammaglobulin is extracted from a fraction isolated by fractionation with ethanol in the presence of a carbohydrate, and after reducing the content of contaminants with PEG, it is applied to an anionic resin exchange column, an effluent being obtained in which the PEG content is subsequently reduced by ultrafiltration and which is concentrated in order to carry out sequentially an optional treatment at an acid pH and at least one of the following steps of viral inactivation, consisting of pasteurisation and a treatment with solvent/detergent, the product afterwards being precipitated and washed with PEG in order to eliminate any chemical viral inactivation reagents and then, by solubilisation and change of pH, the protein contaminants, and finally purified by ultrafiltration to reduce the volume and the PEG content, then carrying out an optional virus filtration and subsequent concentration.

47 Claims, No Drawings

PROCESS FOR THE PRODUCTION OF VIRUS-INACTIVATED HUMAN GAMMAGLOBULIN G

The present invention relates to a process for the production of virus-inactivated human gammaglobulin G. The starting material for obtaining the gammaglobulin (human immunoglobulin G or IgG) of the invention comes from a pool of donations (greater than 1000) of human plasma forming a polyvalent mixture of antibody activities, the individual units of which have been tested against the typical markers of infectiousness (HIV, virus hepatitis B, C).

The administration of gammaglobulin can be effected by the intramuscular route or, more effectively, by the intravenous route. This second route has great therapeutic advantages compared with the first, such as its greater efficacy, but it may cause serious side effects. Only the products obtained in conditions which do not promote denaturing and with an adequate degree of purity are acceptable for the intravenous route.

The preferred and most effective clinical use of the product of the invention is the intravenous route, the therapeutic indications of which are those recognized for this type of products (IgG) which have similar characteristics of composition and molecular structure. The most common therapeutic indications of the IgG of the invention are confined to three general groups of pathologies: primary immune-deficiencies (lack of humoral response), secondary (or acquired, for example as a result of virus infection) immune-deficiencies, and those of autoimmune origin (development of auto-antibodies). With regard to the first group, the IgG of the invention is potentially useful against common variable immune-deficiency, deficit of sub-classes of IgG, absence of IgA, and others. The most common illnesses belonging to the second group would be those produced as a result of infection by viruses and bacteria (HIV or human immune-deficiency virus, cytomegalovirus, herpes zoster, hepatitis B virus, etc.), neonatal sepsis, etc. The identified indications of IgGs in illnesses having an autoimmune component are increasing all the time, outstanding among these being idiopathic thrombocytopenic purpura (ITP) which contributes to the destruction of the platelets, Kawasaki syndrome, etc.

With regard to the previous antecedents, concerning preparation and infusion of gammaglobulin, these go back to the end of the 40s through the materials produced by the known method of plasma fractionation of Cohn (Cohn E. J., Strong L. E., et al.) Separation into Fractions of the Protein and Lipoprotein Components. J. Am. Chem. Soc. 68, 459–475; 1946), or later with the modifications introduced by Kistler-Nitschmann (Kistler P. and Nitschmann Hs. Large Scale Production of Human Plasma Fractions. Vox Sang. 7: 414–424; 1962). The additional purification introduced by Oncley (Oncley J. L., et al. J. Am. Chem. Soc. 71: 541–550: 1949) starting from an intermediate material obtained from the plasma fractionation of Cohn gave rise to the known Cohn-Oncley method, still in force as a method for general purification of gammaglobulin, owing to the fact that both use ethanol in the cold as a concentration medium. The gammaglobulin produced by any of the earlier methods shows a molecular distribution having a significant content of polymerised or aggregated forms having a high molecular weight, when analysed by way of a high resolution gel of exclusion in column (HPLC). Similarly, the liquid presentations thus obtained may offer little stability, opalescence or turbidity being observed during storage, fragmentation and polymerisation of the gammaglobulin molecules, a tendency towards reduction of the activity of some of the more labile antibodies, spontaneous generation of anticomplementary activity, etc.

The problems concerning the therapeutic use of gammaglobulin by intravenous infusion go back to the first preparations obtained by the Cohn-Oncley method, including its many variants, which caused the appearance of adverse reactions (anaphylactoids) with a very high incidence, especially in agammaglobulinaemic patients receiving it (up to 90% of cases). The reactions described were associated with a reduction of the complement of patients treated by this route (Barandun, S. et al. Vox Sang. 1962; 7:157–174).

It was observed that the gammaglobulin obtained by alcoholic fractionation has a notable capacity for fixing the complement spontaneously, as a result of the denaturing of the protein produced during the process of obtaining it, and especially by the generation of gammaglobulin aggregates which gave rise to forms having a high molecular weight, which would optionally act as antibody-antigen complexes having the capacity to freely fix the complement.

The separation of the gammaglobulin aggregates by conventional techniques, either those of ultra-centrifuging or exclusion chromatography (permeation in gel), make it possible to obtain a product having a low anticomplementary activity tolerable by the intravenous route (Barandun et al., above). However, the techniques of ultra-centrifuging or permeation in gel cannot be scaled up for industrial production of a batch size of the order of a few kilograms of gammaglobulin (and not even to the scale of grams in the case of ultra-centrifugation).

On the other hand, the production of gammaglobulin by means of alcoholic fractionation, once freed of the aggregated compounds of high molecular weight, could easily recover its anticomplement activity in the final operations of the process (sterilisation, lyophylisation) or during its storage (in liquid form).

In order to avoid the serious drawbacks of the classic preparations obtained by the Cohn-Oncley method of precipitation with ethanol (or its variants), the present state of the art substitutes or incorporates additional steps which improve the stability and the tolerance of the product for its intravenous infusion.

Polson et al. (Poison, A. et al. Biochim. Biophys. Acta, 82: 463–475; 1964) described a process for fractioning human plasma by means of ethyleneglycol polymers, throughout of which it is possible to separate a purified fraction of gammaglobulin. Coval, L. (U.S. Pat. Nos. 4,093, 606 and 4,165,370, priority 1976 and 1978 respectively) incorporate polyethyleneglycol (PEG) as purification agent for obtaining intravenous gammaglobulin starting from a material separated from the Cohn fractionation (fraction II or II+III). Subsequently there were published equivalent purification processes with polyethyleneglycol, such as that described by Uemura Y., et al. (Spanish Patent No. 506679, applied for in 1981), or similar ones with the only difference that optional pasteurisation of the material which contains the gammaglobulin is introduced, prior to or subsequent to purification with polyethyleneglycol, as also revealed by Uemura Y., et al. (Patent EP 0246579, priority 1986). Also related were chemical methods of virus inactivation with organic solvents and detergents, very efficient against virusses with a lipidic coating, having been applied to proteins derived from human plasma by Neurath et al. (U.S. Pat. No. 4,540,573).

Processes have been described for obtaining gammaglobulin acceptable for intravenous administration using a treatment with enzymes, pepsin (Spanish Patent No.

86115016 and French Patent 2382 M), plasmin (German Patent DE 2752694), immobilised trypsin (Spanish Patent P 0530592), or by treatment at a moderate acidic pH (Acta Chemica Scandinavica, 22: 490–496; 1968) (Barandun S., et. al., above).

Other processes described for obtaining gammaglobulin tolerable by the intravenous route are based on chemically and partially modifying the IgG molecules, treating them with reducing agents (Wiederman et al. Proc. Soc. Exp. Biol. Med., 113: 609–613; 1963), alcoholisation (Spanish Patent No. 412552), alkylation (Spanish Patent No. 0533908) and sulphonation (Yamanaka T., et al. Vox Sang., 37: 14–20; 1979).

Based on ion exchange chromatography, processes have been described which eliminate the undesirable contaminants from the starting materials which are used to obtain gammaglobulin (U.S. Pat. No. 3,869,436, Spanish Patent No. 518181, EP 91300790 and WO 94/29334). Sarno M. E., et al. (Patent EP 0440483) discloses a combination of techniques useful for facilitating the intravenous preparation of the product, based on ion exchange chromatography and diafiltration at a weak acid pH.

The final formulation of the preparation is especially important for the adequate stabilisation of the product. The lyophilised preparation was that initially accepted by the state of the art when the product exhibited a minor alteration during its storage. Compositions for lyophilised product, acceptable for intravenous administration, were published which provide protection against the denaturing of the gammaglobulin, principally during the lyophylisation operation (Spanish Patent No. 525246), using carbohydrates, polyols, glycol or derivatives, amino acids, and also the presence of serum albumin.

More recently there have been described stable liquid formulations which use carbohydrates, in an aqueous medium having a very low ionic strength and a pH of 4.25 (U.S. Pat. No. 4,396,608), or at a weakly acid pH of 5–6 (Patent EP 0278422).

Therefore, according to the state of the art, the intravenous gammaglobulins marketed to date belong to one of the following three groups, which are distinguished basically by their preparation process:

1st generation, obtained by enzymatic methods (pepsin, trypsin, plasmin, etc.)

2nd generation, chemically modified (reduction, sulphonation, alkylation, treatment with beta-propiolactone, etc.)

3rd generation, corresponding to intact molecules of IgG (diafiltration at a low pH, chromatography, precipitation with polyethyleneglycol, formulation at an acid pH and low ionic strength).

The intravenous administration of the current preparations does not give serious intolerance reactions, although each of them has some type of therapeutic drawback, inconvenience or contra-indication. Thus, the enzymatically treated products have a shorter mean half-life in vitro (about 8 days) than normal gammaglobulin G (20 to 25 days), null opsonisation capacity (absence of the Fc fragment), and may exhibit fragmentation and a very limited quantity of the sub-classes IgG 3 and IgG 4.

The gammaglobulins obtained by chemical modification have a mean half-life in vitro (10 to 15 days) less than the physiological, maintain the opsonisation capacity and molecular integrity, but depending on the treatment may suffer a reduction in their bacteriolytic capacity and form new antigen determinants (treatment with beta-propiolactone).

More recently, intact gammaglobulins have been obtained by methods which avoid the denaturing of the IgG molecules. In some cases, the production methods developed may likewise be able to be coupled to fractionation with ethanol, so that it is feasible to take as starting material one of the gammaglobulin-rich fractions separated by the Cohn, Cohn-Oncley or Kistler-Nischmann methods, for example.

According to the processes disclosed to date, for the preparation of intact IgG, recourse is had to moderate treatment at an acid pH, diafiltration at an acid pH, stabilisation of the IgG molecules at a low ionic strength and a pH of 4.25. With these methods it is optional to sufficiently reduce the level of aggregated forms of IgG (high molecular weight polymers and intermediate oligomers up to and including dimers) the proportion of monomeric IgG being increased. The final liquid formulation at a pH of 4.25 inhibits the re-aggregation of the IgG molecules during storage, remaining stable in solution (but only at the conservation temperature of 2° C.–8° C.) with a sufficiently low level of the anticomplementary activity.

The main problem of the liquid preparations obtained exclusively by acidification treatments is the reversibility of the inhibitory effect on the anticomplementary activity induced by the reduction in pH, said activity being recovered again on re-establishment of the pH conditions of the medium at or close to physiological values. On the other hand, the innocuousness of intravenous infusion of large volumes of gammaglobulin preparations formulated at such an acid pH value (pH 4.25) is questionable enough (in the new-born and patients with renal disorders).

In another purification processes, cationic and/or anionic, ion-exchange resins are used, which are applied to the solutions arising from the intermediate precipitates of the Cohn or Cohn-Oncley ethanolic fractionation (fractions II+III or fraction II, preferably), or directly to the plasma pool, avoiding the fractionation with ethanol. The gammaglobulin thus purified can be combined with one of the earlier acidification processes (intermediate or in formulation) or another equivalent process for its liquid formulation, otherwise should keep its stability in lyophilised form.

The ion-exchangers used by the prior art consist of ligands of strong anionic type (quaternary ammonia-ethyl: QAE) and weak anionic type (diethylamino ethyl: DEAE), or strong cationic (sulphopropyl: SP) and weak cationic (carboxymethyl: CM). The ligands are covalently immobilised on insoluble supports or matrices, the composition of which may be: silica (ceramics), acrylic (polyacrylamides, polystyrene), carbohydrate (cellulose, dextran, agarose). Principally, those formed by dextran (Sephadex, of Amersham-Pharmacia) or agarose (Sepharose, of Amersham-Pharmacia) are the most efficient and most used. However, they have some drawbacks still not remedied by the prior art, and refer, depending on the case, to the large quantity of resins necessary for effective separation of the contaminant proteins and their impact with respect to the recovery of gammaglobulin G and on the correct distribution of sub-classes, essentially IgG 4. The compromise situation created between purification (elimination of contaminant proteins: IgA, IgM and others) and recovery of IgG (IgG4) is resolved, depending on the case, in favour of one side or the other, hence the efficacy and therapeutic quality of the gammaglobulins marketed may be very different from one another.

By means of fractionation of the plasma with PEG, or by precipitation with PEG starting from an intermediate Cohn fraction or equivalent, such as fraction II+III, it is feasible to obtain a lyophilised gammaglobulin that can be administered intravenously, but may prove to be insufficiently stable in the liquid state. If an intermediate pasteurisation treatment is included (prior to precipitation with PEG) a significant molecular aggregation occurs, including in the presence of stabilisers (such as sorbitol, for example), due principally to the presence of unstable proteins. Since the higher aggregates must be totally eliminated in subsequent stages, this causes a significant reduction in the product recovery. If starting from more purified fractions (fraction II, or equivalent), the high molecular weight aggregates present in the starting material, or generated by pasteurisation, are not essentially separable by means of precipitation with PEG in the conditions established by the techniques currently described. These indicate concentrations of PEG of 4–5% at a pH of 4–6 (Coval L., above) and 4–10% of PEG at a pH of 4.8–6.5 (Uemura Y. et al., above) which would be valid exclusively when the gammaglobulin was in the presence of other accompanying proteins (present in fraction II+III, for example) capable of co-precipitating together with the high molecular weight aggregates.

The method of the present invention substantially improves the current state of the art, since by means of an innovative combination of process steps, carried out under the precise conditions which are detailed in the present invention, the result produced is a gammaglobulin virtually devoid of protein contaminants detectable by using the most sensitive analytical techniques, and without compromising the molecular integrity or the recovery and distribution of IgG sub-classes, maintaining a low capacity for spontaneously fixing the complement.

The safety of the product, with regard to the potential risk of virus transmission, is maximum in the process described now by the inventors. Into this have been introduced the methods of pasteurisation in the presence of a sugar-alcohol (for example sorbitol) and/or of the solvent-detergent with tri-n-butyl phosphate (TnBP) and polysorbate-80 (Tween-80) or equivalents, as principal steps of controlled virus inactivation, which are highly efficient and complementary. To these steps have been added the viricidal action of an optional prior treatment at an acid pH, which would eliminate or attenuate the virus content before proceeding to the principal inactivation steps. It is also possible for the solution of the product to be nanofiltered for virus retention, during the treatment at an acid pH or preferably diafiltered in bulk prior to the final concentration and formulation.

The combination of the previous methods of virus elimination provide the product with the maximum viral safety and surpasses the state of the art of the products with a single individual inactivation step, with the great industrial advantage that the steps (optionally up to four) of the method of the invention can be carried out consecutively, and therefore in a single inactivation zone or single safety level.

The inventors discovered, surprisingly, that starting from an intermediate material from the Cohn alcoholic fractionation (preferably fraction II+III), it was optional to extract substantially all the gammaglobulin in the presence of a carbohydrate (preferably sugar-alcohol), adjusting the conditions for extraction of the IgG according to the dilution volume, pH and ionic strength, and to separate a major part of the accompanying proteins by precipitation with PEG. The resulting supernatant (filtrate) was a liquid devoid of particles and colloids, which made optional the subsequent highly efficient adsorption in an ion-exchange column, the resultant effluent being substantially devoid of undesirable contaminants (IgA, IgM, proteolytic enzymes, etc), without compromising the yield of IgG or the distribution of sub-classes.

More surprisingly, the inventors demonstrated that in the highly purified column effluent and under the specific conditions proper to the invention, it was optional to greatly reduce the residual PEG and ethanol present by ultrafiltration, and to concentrate the protein as desired. It permitted subsequent viral inactivation treatments (optional treatment at an acid pH, pasteurisation, solvent/detergent) linked together and without producing deep denaturation (detectable by the absence of formation of particles and colloids), nor aggregation (only 1–2% of soluble polymers having a high molecular weight). This reduced polymer content is attributable to the presence of a carbohydrate (among other components) which stabilise the solution in all the operations which precede pasteurisation.

The inventors also discovered, very surprisingly, a method different from those described by the prior art for eliminating or reducing the reagents of viral inactivation by solvent/detergent, added in the preceding step, based on precipitating the gammaglobulin with PEG and maintaining the chemical reagents diluted in solution and at a low temperature to assist the reduction of the mycelia content. Then, separating the precipitate by tangential flow microfiltration, and immediately afterwards proceeding to wash the material retained in order to be able to displace said reagents totally. The precipitate was solubilised directly in the same micro-filtration equipment by bringing it into contact with a suitable solution and without the need for physical manipulation.

The solution obtained by the process described, in spite of containing only 1–2% of polymers, was not considered acceptable for intravenous administration. The inventors observed, surprisingly, that by suitably diluting the previous solubilised precipitate, such that specific concentrations of PEG and of the carbohydrate (added previously) were reached, the high molecular weight aggregates were insolubilised when a specific pH range was reached, and these separate totally from the majority of the monomers and dimers of the solution. It was demonstrated that the concentration of the carbohydrate (preferably a sugar-alcohol), and also that of the PEG, were decisive for avoiding the co-precipitation of monomers/dimers of IgG and for recovering the maximum IgG in the solution. The precipitate formed could be separated easily by tangential microfiltration or by conventional filtration. The resultant filtrate, devoid of aggregates, diafiltered by ultrafiltration under actual process conditions which form part of the invention, gave rise to a product which could optionally be filtered by virus retention membranes and finally concentrated (to 5% or 10% of gammaglobulin) with the absence of, or a very low content of, the chemical reagents added in the process.

The method of the invention surpasses the present state of the art by completely remedying the customary deficiencies of the commercial gammaglobulins previously cited. The gammaglobulin obtained (at 10% concentration of IgG) is substantially devoid of (or there cannot be detected): polymers or high molecular weight aggregates (monomers+dimers >99%, and preferably >99.9%); different protein contaminants of gammaglobulin; IgA (<0.003 mg/ml); IgM (<0.002 mg/ml); PKA (<2.77 IU/ml) and kallikrein; plasmin and plasminogen; albumin; tri-n-butyl phosphate (<3.6 ppm); polysorbate-80 (<50 ppm); PEG-4000 (<500 ppm). It has a high content of the more labile sub-classes IgG 3 and IgG 4, and molecular integrity (fragment Fc >100%), with a low capacity for spontaneous activation of the complement (ACA<1 CH50/mg protein). The liquid formulation with sorbitol is stable, for at least 2 years, both at 2° C.–8° C. and up to 25° C. Together with the excellent product characteristics, there is added the maximum safety provided with regard to the risk of virus transmission through a plasma derivative, being in mind the potential inactivation capacity of the solvent/detergent, pasteurisation, optional incubation at an acid pH, and optional virus filtration (nanofiltration), and also the process steps which contribute to reducing the viral load (precipitation with ethanol, precipitation with PEG, adsorption by ion charge, etc.). On the other hand, it is important to point out that the entire process can be carried out in less than 5 days in suitable installations and the final yield of IgG may exceed 4.5 g per liter of starting plasma.

The process of the present invention will be explained in detail below.

The process starts from a precipitate rich in IgG obtained by ethanolic fractionation of human plasma, preferably from fraction II+III of the Cohn method. Each kilogram of said precipitate is suspended in an aqueous solution, preferably at a rate of 5 kg to 25 kg of a solution which contains a carbohydrate, preferably a sugar-alcohol, and more preferably sorbitol at a concentration (w/v) comprised between 2% and 10%. As a pH buffer, phosphate and acetate ions are preferably used, at a concentration such that the pH of the aqueous suspension of the fraction II+III is between 4.8 and 5.8, and the conductivity does not exceed 2 mS/cm. After a minimum agitation time, preferably greater than 1 hour, the majority of the globulins extracted accompanying the IgG are precipitated with PEG having a nominal molecular weight of preferably 4000, in a concentration range (w/w) of 2.5% to 5.5%, and at the preferred temperature of 2° C.–8° C. Immediately afterwards, and before proceeding with the separation of the precipitate, there is preferably added an adsorbent of lipids and lipoproteins, such as, for example, bentonite, and also preferably a filtration coadjuvant, such as, for example, Hyflo-supercel or Celite (both marketed by J. Manville) or equivalents, such that filterability of the suspension is aided. The precipitate formed is preferably retained by press filtration using depth cellulose filter sheets or plates (grades, 50 SA of the Cuno brand, or KS-80 or K-200 of the Seitz brand, or equivalents) such that the filtrate obtained has a turbidity of less than 5 NTU (nephelometric turbidity units). Optionally, the precipitate may be separated in combined form by centrifuging and filtration. If the precipitate has been retained by press filtration, it may be washed with a suitable solution adjusted to a concentration of PEG, phosphate-acetate ions and pH equivalent to the conditions of adjustment of the precipitation, thereby facilitating a higher recovery of IgG.

The filtrate obtained is brought to a pH of between 5.7 and 6.3, preferably by the addition of a dilute solution of sodium hydroxide, and is subjected to clarification in line with injection into an ion exchange column.

The ion-exchange column contains resins with anionic ligand, preferably those of the diethyl aminoethyl (DEAE) type, coupled to an insoluble matrix of the agarose, or preferably DEAE-agarose and commercially known as Sepharose, preferably those which have a high dynamic capacity (FF or fast-flow). The column used is preferably of the radial flow distribution type, being preferably with a length (or bed height) of between 8 cm and 15 cm. The filtrate is adjusted to a flow rate of preferably less than four column volumes per hour, being injected into the column in which the resins are packed, until the solution is exhausted, such that the quantity introduced, equivalent to initial starting material (preferably fraction II+III), is preferably between 1 g and 2.5 g per ml of resins. Once the loading of the solution is completed, the column is preferably washed with 2.5 to 4.5 column volumes of a solution having an ionic strength and pH similar to the solution of the product previously injected.

The liquid effluent during loading and washing or excluded from the column (non-adsorbed fraction), is ultra-filtered with the aim of reducing the PEG content and of obtaining a suitable concentration of protein to carry out the subsequent steps of viral inactivation. The preferred ultra-filtration membrane has 100 kDa of nominal molecular cut-off, and is preferably constructed with polysulphone (or its derivatives), of the commercial brands Millipore or Pall-Filtron. Initially, the solution is adjusted to a pH of between 5.0 and 5.5 by the addition of a weak acid (for example dilute acetic acid) and is maintained at a temperature of 2° C.–8° C., filtration being started at a transmembrane pressure of preferably between 1.5 bar and 2 bar. After reducing the volume, preferably to half the initial volume, diafiltration is carried out preferably at constant volume, preferably using between 1 and 3 volumes of water for injection. Then, the pH of the solution is brought to 4.0–4.8, and preferably between 4.2 and 4.6, by the addition of a mineral acid. The transmembrane pressure is adjusted to a value below 1.2 bar, and preferably between 0.5 bar and 1.0 bar, and optionally concentration is again carried out by means of reduction of the current volume to half. Diafiltration is carried out, preferably by the addition of not less than 3 volumes of a solution which contains a sugar-alcohol, preferably sorbitol at a concentration (w/v) of between 2% and 10% adjusted to pH 4–5 with acetic acid. Finally, protein concentration is carried out to the required value, preferably to an optical density (at 280 nm) of more than 45 AU (absorption units), subsequently being sterilised by filtration, preferably using absolute membrane of 0.22 microns. Optionally, the solution, sterilised and stabilised (with the sugar-alcohol originary from the diafiltration solution), can be kept for a long period of time at a temperature of 2° C.–8° C.

At the time of continuing the process, the solution cooled to 2° C.–8° C. may optionally be brought to an acid pH, preferably between 3.75 and 4.25, by the slow addition of a dilute mineral acid at a temperature of 2° C.–8° C. Preferably, the optionally pH-adjusted solution is incubated at 2° C.–40° C. for 0.5 hours to 48 hours, and more preferably at a pH of between 3.95 and 4.05 between 35° C. and 38° C. for 1 hour to 4 hours, in the presence of the sugar alcohol, preferably sorbitol at 2%–10% (w/v) added in the prior diafiltration. Also optionally, and during the treatment at an acid pH for example, the solution may be virus-filtered through a nanometric pore membrane, preferably having a pore size of between 15 nm and 50 nm, such as, for example, 50 nm filters (DV50 of the Pall brand), 35 nm (BMM-Planova 35N of the Asahi brand), 20 nm (DV20 of the Pall brand), 15 nm (BMM-Planova 15N of the Asahi brand), or having equivalent pores.

When the optional treatment at an acid pH is completed, the temperature is brought to 2° C.–8° C. and the solution is rendered alkaline preferably by the addition of a dilute strong base, the pH reaching a value of between 4.7 and 5.2. Immediately afterwards, a carbohydrate is added as stabiliser, preferably a sugar-alcohol, and more preferably sorbitol, at a preferred final concentration (w/w) of between 25% and 35%. Pasteurisation is carried out at 60° C.–62° C. for 10 to 12 hours, preferably in both cases.

The solution is then diluted with water for injection until the concentration of the carbohydrate, or preferably of the sugar-alcohol, is below 25% (w/w) and the protein is between 1% and 3% (w/v). Once the solution is cooled to room temperature, a concentrated solution of a mixture of solvent/detergent is added, formed preferably by the alkylphosphate reagents and non-ionic detergent, and more preferably by tri-n-butyl phosphate and polysorbate-80, such that the final concentration (w/v) is preferably 0.3% and 1% of the two reagents, respectively. Incubation is carried out at 24° C.–28° C. for a period of between 4 and 8 hours, preferably in both cases. (The virus-inactivated solution will from then on be in an exclusive viral security area for inactivated products, within which the remaining operations are carried out).

The solution is subsequently diluted with cold water for injection, preferably adding between 1 kilogram and 2 kilograms of water for every kilogram of solution, substantially all the protein present being precipitated by the addition of a sufficient amount of PEG (preferably having a molecular weight of 4000), bringing the solution to a final concentration (w/w) of between 12% and 17% of PEG, and previously adjusting the pH between 7.0 and 9.0, preferably between pH 7.8 and 8.4, at the preferred temperature of 2° C.–8° C. After a prudential homogenisation time, preferably more than 1 hour (by stirring) and optionally being left to stand, the retention of the precipitate is started in equipment for tangential flow filtration (TFF) membrane. The filtered liquid being separated contains, among others, the inactivation reagents used in the earlier solvent-detergent step. The preferred tangential filtration membrane is that constructed with polyvinylidene fluoride (PVDF) of the Millipore brand (Prostak configuration or equivalent models). Other materials compatible with the reagents which the solution contains, such as polysulphone, may optionally be used in place of PVDF. The pore size of the filtration membrane is preferably between 0.1 micron and 0.45 micron. The separation of the filtrate is carried out at a transmembrane pressure below 1.5 bar.

Once the volume of the initial suspension has been reduced preferably up to 4 to 8 times, washing of the precipitate retained is started by the addition at constant volume of a solution which contains PEG, preferably at the same concentration as that used in the previous precipitation, and preferably the same carbohydrate used in pasteurisation, preferably a sugar-alcohol, preferably at a concentration (w/w) of between 5% and 20%. After using preferably between 4 volumes and 6 volumes of the above washing solution, the residue is solubilised with an acid solution at a pH below 5.5 which preferably contains the same carbohydrate used in the previous steps. The solution is preferably formed by acetic acid between 1 mM and 10 mM to which is added a sugar-alcohol at a concentration (w/w) of preferably between 5% and 20%, and is adjusted with an alkali to pH 4.0 to 4.5. The temperature of the solution does not exceed 37° C., and is preferably between 2° C. and 8° C. An amount of acid solution for solubilisation of between 2.5 and 4.5 times the amount of residual suspension is added. In this way the final concentration (w/w) of PEG is between 2% and 4%, and preferably between 2.8% and 3.4%, the sugar-alcohol preferably being between 5% and 20%. The solubilisation solution is left in contact with the retained precipitate by means of recirculation until it is completely dissolved.

The solubilised product is brought to a pH of between 7.5 and 8.5, and preferably between 7.8 and 8.3, by the addition of a dilute alkaline hydroxide or an acceptable weak base, the preferred temperature being 2° C.–8° C. After homogenising, the precipitate formed can be separated preferably through the same TFF equipment used earlier, the filtrate being recovered as the product of interest. Another way of proceeding is by substitution of the TFF equipment by disposable filters of membrane, plate or multilayer cartridges (depth).

The filtrate obtained, free of high molecular weight aggregates, and also of the major part of the reagents of the solvent/detergent, is brought to a pH of preferably between 5 and 6, by the addition of dilute acid.

The solution is ultrafiltered with the aim of reducing the content of PEG and of other low molecular weight compounds, and of obtaining a suitable concentration of protein for adjusting the product to the final formulation. The preferred ultrafiltration membrane has 100 kDa of nominal molecular cut-off, and is preferably constructed with polysulphone (or its derivatives), of the commercial brands Millipore and Pall-Filtron. Ultrafiltration is started at a transmembrane pressure of preferably between 1.5 bar and 2 bar. After reducing the volume, preferably to ½ to ⅓ of the initial volume, diafiltration is preferably carried out at constant volume, preferably using 1 volume of water for injection. Then, the pH of the solution is brought to 4.0–4.8 and preferably between 4.2 and 4.6 by the addition of a dilute mineral acid. The transmembrane pressure is adjusted to a value below 1.2 bar, and preferably between 0.5 bar and 1.0 bar, and the solution is concentrated again by means of reduction of the current volume to ½ to ⅓ of the initial volume. Diafiltration is carried out preferably by the addition of not less than 5 volumes of a solution which contains a sugar-alcohol, preferably sorbitol at a concentration (w/v) of between 2% and 10% adjusted to pH 4–5 with acetic acid. The previous solution, diafiltered and preferably concentrated to 1%–3% (w/v) of protein, is pH-adjusted to between 4.4 and 5.0 if necessary, and preferably heated to 25±5° C. Afterwards, an optional virus filtration is carried out with retention membranes with nanometric pore equal to or below 50 nm nominal, and preferably approximately 20 nm nominal (DV20 of the Pall brand) with a protein recovery of more than 90% and a productivity of more than 1 kilogram of protein/m$^2$ of filtration area in less than 24 hours of process time, or also preferably those ranging between 15 and 20 nm nominal (BMM-Planova 15N or P21, both of the Asahi brand; VNF "Parvo" of Millipore) with protein recovery of more than 80%.

Finally, protein is concentrated by ultrafiltration with membranes of 100 kDa, or smaller size of nominal molecular cut-off, up to the value required, preferably up to a final optical density (at 280 nm) of approximately 75 AU, to obtain a concentration of IgG of 5%, or about 150 AUs for the 10% concentration.

The solution, suitably formulated according to the concentration of the stabiliser (sugar-alcohol) of the diafiltration solution, is brought to a pH of 5–6 and is clarified by depth filters (grade 90LA of the Cuno brand, or equivalent). It is sterilised by absolute filtration using a 0.22 micron membrane and then it is dosified into glass containers. The product is submitted a minimum quarantine of 15 days at 25° C., the solution proving to be translucent and devoid of visible particles. The product is stable at temperatures of 2° C.–8° C. and up to 25° C.

Several examples of application are described below by way of non-limiting information concerning the invention:

EXAMPLE 1

90.0 kg of the fraction II+III paste (batch No. 9003; equivalent to 1490.9 liters of starting plasma), obtained according to the Cohn method, were suspended in 1323 kg of an extraction solution formed by 5 mM disodium phosphate and sorbitol at 5% (w/v) adjusted to pH 4.83 by the addition of 23.0 liters of 0.5 M acetic acid. After 1 hour's stirring and after adjusting the pH of the suspension to 5.05 by the addition of 1.4 liters of 0.5 M acetic acid, it was left for 2 more hours' stirring at between 2° C. and 6° C. It was established that the pH had not varied and the conductivity was 1.05 mS/cm. Then, with sufficient stirring, 135.5 kg of a solution of PEG-4000 (at 50%) were added. Immediately afterwards, 3600 g of bentonite were added, and after readjusting the pH to 5.03 with 2 liters of 0.5 M acetic acid, the whole was left to precipitate while standing for 4 hours. Just before proceeding with the separation of the precipitate by filtration, Hyflo-supercel was added, while stirring, at a rate of 32.5 g for every kilogram of suspension, and the mixture was immediately filtered through depth plates (Cuno brand, grade 50 SA) using a press filter suitable for retaining the precipitate. On the one hand a total of 1768 kg of filtered liquid (which included a post-wash), were collected, being transparent and slightly yellowish, having an optical density (at 280 nm) of 8.38 AU and a turbidity of 2.7 NTU, and on the other hand 188.3 kg of precipitate were obtained, which were discarded.

The previous filtered solution was adjusted to pH 5.92 by the addition of 8000 ml of 0.5 M sodium hydroxide, the conductivity of the resultant solution being 1.113 mS/cm.

Sufficiently in advance, a radial flow ion exchange column (Sepragen brand) was prepared which contained 50 liters of DEAE-Sepharose FF resins (of Amersham-Pharmacia), packed radially with a bed thickness of some 10–12 cm. The column was equilibrated with a solution of sodium acetate and acetic acid having an ionic strength and pH equivalent to the solution of the product. The solution of the product was then injected into the column, being filtered in line during loading, at a flow rate such that the duration of the process was 12 hours and 18 minutes. Finally, a post-wash was carried out with 180 kg of the equilibration solution. A total of 1930 kg of the column effluent (fraction not adsorbed) were collected, which essentially contained IgG as the only protein component, having a pH of 5.99, conductivity of 1.081 mS/cm, turbidity of 2.4 NTU and optical density (at 280 nm) of 6.95 AU.

The solution was adjusted to a pH of 5.19 by the addition of 13 liters of 0.5 M acetic acid and was concentrated to 1030 kg by ultrafiltration with membranes of 100 kDa molecular cut-off of the brand Biomax A-2 (of Millipore), at a transmembrane pressure of 1.95–2.20 bar and at a temperature of about 4° C., the filtrate having an optical density (at 280 nm) <0.150 AU being discarded. Immediately afterwards, diafiltration was carried out at constant volume with 2054 kg of water for injection, the final conductivity of the solution retained being 0.164 mS/cm. Then, without stopping ultrafiltration, it was brought to a pH of 4.26 by the addition of cold 0.2 M hydrochloric acid and diafiltration was continued at constant volume, on this occasion with respect to 3833 kg of a solution of sorbitol at 5% (w/w) and 2 mM acetic acid adjusted to pH 4.12, at a transmembrane pressure of 1.05–1.10 bar and at about 4° C. Finally, the residue was concentrated until its optical density (at 280 nm) reached 72.7 AU. Then the equipment was washed down with the diafiltration solution such that 233.5 kg of the bulk were obtained, with an optical density (at 280 nm) of 55.5 AU, followed by sterilisation by filtration through a 0.22 micron pore membrane (type CVGL filter of Millipore).

The sterilised solution, cooled to 6.0° C. was brought to pH 4.00 by the slow addition of 7250 ml of cold 0.2 M hydrochloric acid, monitoring the pH during said addition. Afterwards, the bulk solution was rapidly pre-heated in a tank with heating jacket while stirring, being thermostatted at 36.5° C.–37.3° C. for 4 hours.

With the treatment completed, the solution was cooled and stabilised by the addition of 114.3 kg of solid sorbitol, being stirred until completely dissolved. The pH of the solution was brought to 4.85 by the slow addition of 7000 ml of cold 0.2 M sodium hydroxide. 388.8 kg of the solution were obtained, having a turbidity of 1.41 NTU and an optical density (at 280 nm) of 36.0 AU. Said solution was immediately pasteurised at between 60.1° C. and 60.7° C. for exactly 10 hours.

It was subsequently cooled and diluted by the addition of 131 kg of cold water for injection, an optical density (at 280 nm) of 27.5 AU being obtained. To the 507 kg of the current dilute solution were added 51.2 kg of concentrated solution of SD, formed by tri-n-butyl phosphate at 3% (w/v) and polysorbate-80 (Tween-80) at 10% (w/v), and incubation was carried out for exactly 6 hours at between 25.8° C. and 26.4° C.

The solution treated with SD was immediately diluted with 841.5 kg of cold water for injection and the pH was adjusted to 8.05 by the addition of 4200 ml of 0.5 M sodium hydroxide, after which there were then added, slowly and while stirring, 654.3 kg of a 50% solution of PEG-4000, being left to precipitate at a temperature of 2.6° C.–3.8° C.

The 2065 kg of the previous suspension of precipitate with PEG were concentrated to 400 kg in tangential flow (TFF) microfiltration equipment through a 0.22 micron pore membrane (Prostak type, of Millipore), at a transmembrane pressure of 0.1–0.3 bar and at 3.6° C.–5.0° C. The suspension of the precipitate retained in the TFF was afterwards washed at constant volume with 2000 kg of a solution containing PEG at 15% (w/w) and sorbitol at 8% (w/w) adjusted to pH 7.97.

The suspension retained was then solubilised by adding 1226 kg of a solution of sorbitol at 14% (w/w) and 4 mM acetic acid adjusted to pH 4.14 with sodium hydroxide. The solution was left in recirculating contact in the TFF equipment until completely solubilised (25 min.). The pH of the solution was then brought to 8.03 by the slow addition of 6500 ml of 0.5 M sodium hydroxide and, after about 15 minutes' stirring, filtration was started with the same TFF equipment (with 0.22 micron pore membranes), the IgG being recovered in the filtrate. After collecting 1474 kg of the filtrate, washing of the suspension retained was started with a solution having composition characteristics similar to the suspension, 1827 kg of total filtrate finally being obtained. The filtrate pool had an optical density (at 280 nm) of 5.66 AU, turbidity of 1.99 NTU and conductivity of 0.158 mS/cm.

The solution was brought to pH 5.53 by the addition of 3000 ml of 0.5 M acetic acid and was concentrated by ultrafiltration with membranes of 100 kDa molecular cut-off (Omega series of Pall-Filtron) at a transmembrane pressure of between 1.75 and 1.95 bar, the volume being reduced to obtain 739 kg. Diafiltration was carried out at constant volume with respect to 736 kg of water for injection, 5600 ml of 0.2 M hydrochloric acid subsequently being added, to pH 4.51. Then the transmembrane pressure was reduced to 0.6–0.9 bar and concentration to 296 kg was carried out, diafiltration being started immediately at constant volume with respect to 2072 kg of a solution of 5% sorbitol (w/w) containing 2 mM acetic acid adjusted to pH 4.16. Once the previous solution was consumed, concentration to an optical density value of 142.5 AU was carried out, in order to prepare two solutions at the concentrations of 5% and 10% of IgG. Said solutions adjusted to pH 5.25 were filtered through a depth plate (Cuno brand, grade 90 LA) and absolute membrane of 0.22 micron pore size (CVGL type, of Millipore), being measured subsequently into 10 ml, 50 ml, 100 ml and 200 ml glass flasks. The final production output of the adjusted solutions, with regard to grams of IgG per liter of starting plasma, was 4.68.

EXAMPLE 2

Several batches of IVIG were processed, each starting from 90 kg of fraction II+III, in the manner described in the method of the invention, the final product (5% IVIG in 50 ml vial) being subjected to rigorous analytical control in order verify the consistency of its quality. The results obtained are shown in Table 1.

TABLE 1

| Parameter | No. of process batches | | | | |
|---|---|---|---|---|---|
| | 9002 | 9003 | 0001 | 0002 | 0003 |
| Protein (%) | 4.6 | 4.5 | 4.7 | 4.8 | N.D. |
| Turbidity (NTU) | 3.3 | 3.3 | 3.0 | 3.1 | 2.8 |
| Sorbitol (%) | 4.75 | 4.85 | 4.9 | N.D. | N.D. |
| Purity (%) | 100 | 99.2 | 99.7 | 99.8 | 99.9 |
| Polymer (%) | 0 | 0 | 0 | 0 | 0 |
| Fractions (%) | 0 | 0 | 0 | 0 | 0 |
| PEG (ppm) | 164 | 311 | 224 | N.D. | N.D. |
| Polysorbate (ppm) | <30 | <30 | 34 | <30 | 40 |
| TNBP (ppm) | <3.6 | <3.6 | <3.6 | <3.6 | <3.6 |
| PKA (IU/ml) | <2.8 | <2.8 | <2.8 | <2.8 | <2.8 |
| ACA (CH50/mg Ig) | 0.68 | 0.76 | 0.75 | 0.66 | 0.63 |
| IgA (mg/ml) | <0.003 | <0.003 | <0.003 | <0.003 | <0.003 |
| IgM (mg/ml) | <0.002 | <0.002 | <0.002 | <0.002 | <0.002 |

N.D., not determined.

The protein was determined by the Bradford technique, using gammaglobulin as control. The turbidity was measured by nephelometry, being quantified with respect to a control solution. The purity of gammaglobulin was determined with respect to the total proteins detected by electrophoresis on a cellulose acetate plate and staining with amide black. The polymers (or molecular aggregates higher than dimers of gammaglobulin) and the low molecular weight protein fractions, were determined by HPLC in an exclusion column in gel (TSK G-3000 SW column of Toyosoda), the % of distribution of the molecular forms indicated being quantified with respect to the total proteins detected, according to the optical density value at 280 nm. The PEG was determined by HPLC filtration column in gel (TSK G-3000 SWXL column) using a refractive index detector. The concentration of sorbitol was quantified by an enzymatic method. The polysorbate-80 was analysed by a colorimetric method and the TNBP by means of gas chromatography. The prekallikrein activator (PKA) was measured by chromogenic testing. The accompanying proteins IgA and IgM were determined by immunonephelometry. The anticomplementary activity (ACA) was determined by the Eur. Phar. method based on the determination of the residual complement after incubation in the presence or absence of the sample.

EXAMPLE 3

In the process of the invention, the chemical viral inactivation reagents added are reduced by precipitation with PEG and washed in TFF equipment. After some investigations, a simple method was established which indirectly permitted monitoring the concentration of said reagents during the TFF process. Bearing in mind that the optical density at 280 nm of the filtrate by TFF proceeds basically from the concentration of the non-ionic detergent and of residues of soluble proteins which escape together with the filtered liquid (PEG does not absorb in the 245–280 nm range), the contribution of protein was corrected by reading at 245 nm, at which a minimum of absorption of protein is detected and which, on the contrary, is very high for the detergent (approximately 14.5 times higher than the protein, in the case of commercial polysorbate-80).

Then, on the basis of readings of optical density at 280 nm and 245 nm, the continuation of the TFF process step was carried out in order to demonstrate the efficacy of the concentration and face washings to the reduction of the SD. According to the measuring procedure developed, the residual SD was quantified corresponding to the process of the previous Example 1. The results are indicated in Table 2.

TABLE 2

| TFF Operation | Quantity of product retained (kg) | Optical Density of filtrate (AU at 280 nm) | Optical Density of filtrate (AU at 245 nm) | Quotient of optical density at 245/280 nm | % of O.D. (at 280 nm) provided by the SD in the Filtrate (1) | % of recovery of the SD in the residue (2) |
|---|---|---|---|---|---|---|
| Start of concentration | 2065 | 0.339 | N.D. | n.a. | n.a. | n.a. |
| End of concentration | 400 | 0.346 | 4.72 | 13.6 | 94 | 95.94 |
| 1st washing volume: 400 kg | 400 | 0.156 | 1.82 | 11.6 | 80 | 36.81 |
| 2nd washing volume: 800 kg | 400 | 0.080 | 0.790 | 9.87 | 68 | 16.05 |
| 3rd washing volume: 1200 kg | 400 | 0.046 | 0.345 | 7.6 | 52 | 7.06 |
| 4th washing volume: 1600 kg | 400 | 0.050 | 0.190 | 3.8 | 26 | 3.83 |
| 5th washing volume: 2000 kg | 400 | 0.030 | 0.137 | 4.5 | 31 | 2.74 |

(1) The % of optical density (O.D.) at 280 nm proceeding from the SD was calculated starting from the quotient of optical density (245 nm/280 nm), divided by the relative absorption factor at 245 nm between SD and protein of 14.5, and multiplied by 100.
(2) The % of recovery of the concentration of SD has been calculated in accordance with the values of O.D. at 280 nm of the corresponding step with respect to that found at the start of concentration (0.339), corrected by the % of O.D. contributed (approximately) by the SD, in accordance with the following expression: % recovery = (O.D. reading (280 nm)/0.339) × (% of O.D. of the SD/100).
N.D., not determined
n.a., not applicable.

The results show the course of the reduction of SD (polysorbate-80) during concentration and washing, there being finally obtained, after 5 washing volumes, only 2.74% of the initial concentration. Consequently, the reduction factor is 36.5 times (100%/2.74%) which corrected by the protein concentration increment of ×5 (2065 kg/400 kg), gives an actual reduction factor of 182 times. Then, and in accordance with the previous values, it is calculated that the concentration of polysorbate-80 in the precipitate retained would be something less than 100 ppm and at an approximate protein concentration of 2%.

Obviously, in order to reach a concentration of <100 ppm at 5% and 10% of protein, the amount of polysorbate present must be reduced more than 5 times. This is optional with the subsequent use of ultrafiltration membranes of 100 kDa, since the concentration of the polysorbate has been reduced sufficiently to a value close to that of mycelia formation, making its separation optional. For the batch of the present Example, the concentration found in the final product (at 5% of IgG) was <30 ppm, below the quantification limit of the analytical technique.

Another two batches, No. 8006 and No. 8007, were processed on a preparatory scale in the same manner as in the present Example 3. Precipitation with PEG was carried out, concentrating and washing in TFF equipment with the same type of membranes used earlier, although on this occasion the number of volumes of washing solution was 4 and 2.5 for batch Nos. 8006 and 8007, respectively. After diafiltration and concentration through membranes of 100 kDa to the final concentration (5% of IgG), the concentration of residual polysorbate of each batch in the final product (IVIG 5%) was determined. The values found (including batch No. 9003) are shown in Table 3.

TABLE 3

| Process No. | No. of Washing Volumes (in the TFF) | Concentration of Polysorbate in final product 5% IVIG (ppm) |
|---|---|---|
| 9003 | 5 | <30 |
| 8006 | 4 | 50 |
| 8007 | 2.5 | 200 |

The results of the previous table 3 show the dependency between the quantity of residual polysorbate and the number of washing volumes, demonstrating that washing by TFF, and under the conditions of the invention, is a key step for the effective reduction of the non-ionic detergent (polysorbate). From the values found it is optional to establish a minimum of 4 washing volumes to ensure residues of less than 100 ppm in the final product.

EXAMPLE 4

Several batches of IgG were processed in accordance with the method of the invention, each starting from 90 kg of fraction II+III. Once the solution purified by a DEAE-Sepharose FF column was obtained, containing approximately 4% of PEG-4000, ultrafiltration was carried out in all cases through a surface of 27.6 m² of polysulphone membranes of the Biomax A-2 brand of Millipore of 100 kDa nominal molecular cut-off, under conditions equivalent to those described in Example 1. The concentrations of protein (according to optical density values) and PEG-4000 obtained are shown in Table 4.

TABLE 4

| BATCH No. | PROTEIN (O.D. 280 nm, in AU) | CONCENTRATION PEG-4000 (mg/ml) |
|---|---|---|
| 9002 | 49.6 | 5.20 |
| 9003 | 55.5 | 4.92 |
| 0001 | 55.9 | 4.92 |

TABLE 4-continued

| BATCH No. | PROTEIN (O.D. 280 nm, in AU) | CONCENTRATION PEG-4000 (mg/ml) |
|---|---|---|
| 0002 | 54.1 | 4.83 |
| 0003 | 54.9 | 5.91 |

The concentration of PEG-4000 was determined by HPLC in an exclusion column in gel and using a refractive index detector.

In another experiment, carried out with one batch (No. 9001) on a preparatory scale (starting from 8 kg of fraction II+III), the process was taken up to the step of the FF DEAE-Sepharose column effluent. Ultrafiltration was carried out through Biomax A-2 membranes of 100 kDa molecular cut-off, under the conditions described in Example 1, adapted to the batch size. On this occasion, differing from Example 1, diafiltration was carried out with respect to sorbitol 5% and without adjusting the pH of the product to 4.2–4.6, diafiltration being carried out at a transmembrane pressure of more than 1.5 bar. At the end, the approximate protein concentration corresponded to an O.D. (280 nm) of 45 AU and the concentration of PEG was 33 mg/ml, or about 6 times higher than the values found in Table 4. The product, processed up to pasteurisation, produced 4% of aggregates, behaving differently from the batches of Table 4, the increments of which were only 1.0%–1.5% of said aggregates.

The results of Table 4 show that the method of ultrafiltration of the invention (relative to pH and transmembrane pressure) fulfils very satisfactorily the aim of efficiently reducing the PEG in order to be able to bring the solution to the protein and PEG concentrations suitable for the subsequent virus inactivation treatments.

EXAMPLE 5

In accordance with the conditions of the invention, several batches of product were processed. These, before carrying out the final ultrafiltration, were brought to a pH of between 5.4 and 5.6 and were concentrated 2.5 times through 100 kDa membranes, at a transmembrane pressure of approximately 1.5–2 bar. They were then washed with 1 volume of water for injection and immediately afterwards the pH was adjusted to between 4.3 and 4.5 by the addition of 0.5 M hydrochloric acid, the transmembrane pressure being reduced to a value below 1 bar, and the volume of their respective solutions was concentrated 2.5 times more. Finally, diafiltration was carried out with 7 volumes of a solution of 5% sorbitol (w/w) which contained 2 mM acetic acid adjusted to pH 4.2 with sodium hydroxide.

The results of the concentration of residual PEG in the final product are to be found in the previous Table 2, with values around 200 ppm (0.02%) at 5% of IgG. Bearing in mind that the PEG and IgG concentrations of the solution prior to ultrafiltration were respectively approximately 3.25% and 4 mg/ml, the PEG reduction factor (corrected according to protein) is 1000–2000 times.

As with the earlier batches, a test was carried out on a preparatory scale in the manner described in the invention according to Example 1 adapted to the batch size. The starting solution was brought to approximately pH 5.0 and concentrated about 4 times through 100 kDa molecular cut-off membranes. Diafiltration was then carried out at constant volume in the same equipment with respect to 9 volumes of 5% sorbitol solution at a transmembrane pressure above 1.2 bar. The PEG and protein concentration values, as well as the PEG reduction factor, are to be found in Table 5.

TABLE 5

| Phase | Concentration of PEG (mg/ml) | Concentration of Proteins (mg/ml) | PEG reduction Factor (corrected) (1) |
|---|---|---|---|
| Starting solution (2) | 32.5 | 3.76 | 1 |
| Solution concentrated 4 times | 55.6 | 14.9 | 2.31 |
| 1st DV with 5% sorbitol | n.d. | 14.9 (approx.) | n.a. |
| 3rd DV with 5% sorbitol | 14.5 | 14.9 (approx.) | 8.74 |
| 5th DV with 5% sorbitol | 11.6 | 14.9 (approx.) | 11.08 |
| 7th DV with 5% sorbitol | 8.4 | 14.9 (approx.) | 15.43 |
| 9th DV with 5% sorbitol and final concentration | 20.5 | 62.8 | 26.18 |
| 5% IVIG (final) | 15.2 | 51.4 | 28.8 |

(1) The reduction factor was corrected according to the protein concentration.
(2) Starting solution corresponding to the filtrate with PEG 3.25% pH 8.
n.d., not determined
n.a., not applicable The results of Table 5 show a discrete transference of PEG through membranes of 100 kDa under the test conditions, due principally to the pH of the medium >4.8 and to the transmembrane pressure >1.2 bar. Therefore it is established that under the actual conditions of the invention the reduction of PEG is much more efficient, in a magnitude of the order of about 50 times (comparison of the reduction factors of 1000–2000 of the previous batches and of 28.8 of the current test).

EXAMPLE 6

The intermediate pasteurisation of the gammaglobulin solution, as well as the subsequent treatment of chemical inactivation by solvent/detergent, scarcely induces molecular aggregation.

Several batches were processed on an industrial scale (each starting from 90 kg of fraction II+III) in accordance with the method of the invention which is described in detail in Example 1. Once incubation at an acid pH had been carried out, the gammaglobulin solution at a concentration of 3.5% was stabilised by the addition of sorbitol to an approximate final concentration of 33% (w/w) and the pH was adjusted to 4.80±0.05 by the addition of 0.5 M sodium hydroxide, the optical density (at 280 nm) being between 35.6 AU and 41.2 AU. Immediately afterwards, it was pasteurised in bulk in a tank with heating jacket, at 60–61° C. for 10 hours. The solution was diluted with cold water for injection to an optical density (at 280 nm) of between 25.9 AU and 28.0 AU, such that the concentration of sorbitol was <25% (w/w) in all cases. It was cooled to 25° C.–26° C. and a concentrated (×10 times) solution of solvent/detergent was added until final concentrations (w/v) of 1% of polysorbate-80 and 0.3% of tri-n-butyl phosphate were obtained. After mixing for about 30 mins, the whole was left to incubate for 6 hours at 25°–26° C.

The content of polymers or high molecular weight aggregates (determined by HPLC) of the solution was determined before and after pasteurising, and after the treatment with solvent/detergent. The generation of collodial particles during pasteurisation was also quantified by nephelometric measurement of the turbidity. The values obtained are tabulated in Table 6.

TABLE 6

| | % OF POLYMERS (OR HIGH MOLECULAR WEIGHT AGGREGATES) | | | TURBIDITY (NTU) | |
|---|---|---|---|---|---|
| BATCH No. | Before pasteurising | After pasteurising | After SD | Before Pasteurising | After pasteurising |
| 9002 | n.d. | 1.23 | N.D. | 1.5 | 1.6 |
| 9003 | n.d. | 1.16 | 1.97 | 1.4 | 1.8 |
| 0001 | n.d. | 1.04 | 1.19 | 5.9 | 1.8 |
| 0002 | n.d. | 1.21 | 1.30 | 2.3 | 2.4 |
| 0003 | n.d. | 1.35 | 1.15 | 1.7 | 2.0 | n.d., not detectable
N.D., not determined

The results show that both the pasteurisation and solvent/detergent treatments carried out under the conditions described of temperature, time and composition of the material (stabiliser, concentrations of protein and PEG, pH, etc.), do not promote the denaturing of the gammaglobulin, bearing in mind the discrete increase in aggregates (<2%) and turbidity. Similarly, at the concentration (approximately 3.5%) of gammaglobulin of the process it is optional to process large quantities per production batch.

EXAMPLE 7

Several tests were carried out to establish the best charge conditions for purification in an ion-exchange resin column.

Starting from the same batch of fraction II+III, several tests were carried out on a preparatory scale, taking 1 kg of the starting material, until the filtered solution from the first precipitation with PEG was obtained, in accordance with the method of the invention.

For each test, the required amount of solution, adjusted to pH 5.9–6.0 was clarified (0.5 micron filter) and thereafter it was injected to a 65 mm or 90 mm diameter column packed with DEAE-Sepharose FF resins (of Amersham-Pharmacia) to a height of 13 cm–17 cm (except in one case which is indicated). Loading was carried out at 2° C.–8° C. and at a flow rate such that the duration was 12–15 hours or 6 hours, depending on the case, all the column effluent being collected and its corresponding washing down carried out in each test with 3.5 column volumes of 10 mM sodium acetate adjusted to pH 5.95+/−0.05 with acetic acid.

Table 7 shows the values for gammaglobulin recovery and the electrophoretic purity (in cellulose acetate) of the effluent.

TABLE 7

| LOADING RATIO (g of fraction II + III/ml of resin) | LOADING TIME (hours) | PURITY OF EFFLUENT (electrophoresis) | | (%) RECOVERY OF GAMMAGLO-BULIN (2) |
|---|---|---|---|---|
| | | Albumin (1) | gamma (%) | |
| 4.0 | 12.15 | (+) | 97.2 | 97 |
| 2.5 | | (−) | 98.7 | 95 |
| 2.25 | | (−) | 98.3 | 105 |
| 1.25 | | (−) | 97.7 | 97 |
| 0.875 | | (−) | 100 | 98 |

TABLE 7-continued

| LOADING RATIO (g of fraction II + III/ml of resin) | LOADING TIME (hours) | PURITY OF EFFLUENT (electrophoresis) | | (%) RECOVERY OF GAMMAGLO- BULIN (2) |
|---|---|---|---|---|
| | | Albumin (1) | gamma (%) | |
| 0.625 | | (−) | 100 | 100 |
| 1.65 | 6 | (+++) | 85.6 | n.d. | n.d., not determined
(1) The symbols: (−) indicates detectable absence; (+) traces; (+++) abundant presence (major contaminant).
(2) Calculation of the recovery in % according to the total protein value (according to O.D. at 280 nm) and purity (electrophoretic) of the column effluent with respect to the initial charge solution.

By applying a charge of 2.5 g of fraction II+III per ml of resins or less, almost total adsorption of the principal contaminants detectable by electrophoresis (absence of albumin) is obtained and without having an adverse effect on the recovery of gammaglobulin, which is excellent in the entire range studied. However, the lower charge range is preferably restricted to 1 g of fraction II+III per ml of resins in order to avoid the use of columns of excessive volume. On the other hand, as could be expected, the flow rate of injection into some agarose matrix resins turned out to be a relevant factor, 12 hours of contact under continuous flow conditions being necessary.

A process (batch No. 9001) was carried out on a preparatory scale (starting from 8 kg of fraction II+III) in accordance with the description of Example 1 but adjusted to the batch size indicated, with the aim of discovering specifically the reduction of some of the principal accompanying proteins by column adsorption. A charge ratio of 1.8 g of fraction II+III per ml of DEAE-Sepharose FF was applied, and a contact time of approximately 12 hours, the concentration of IgA, albumin and transferring being determined both in the column effluent and in the solution before the column. The values obtained are to be found in Table 8.

TABLE 8

| PROTEIN | Before column | After Column | % of recovery (1) |
|---|---|---|---|
| IgA (mg/ml) | 0.16 | <0.003 | <2 |
| Albumin (mg/ml) | 0.248 | <0.0018 | <1 |
| Transferrin (mg/ml) | 0.043 | 0.002 | 5 |
| IgG (mg/ml) | 5.15 | 4.49 | 94.7 |

The quantification of the proteins was carried out by immunonephelometry.
(1) The % of recovery was calculated bearing in mind the absolute amount of protein found in the solutions after and before the column.

It is clear from Table 8 that under the specific conditions of the invention the resins are highly selective and efficient for the separation of the principal proteins associated with IgG which are present in the starting fraction II+III. Only discrete amounts of transferring are detectable in the effluent together with IgG. The high recovery of IgG is a good indicator of the maintenance of the proportion of sub-classes in the column effluent.

EXAMPLE 8

Starting from a highly purified I.V. gammaglobulin solution, the conditions of the step of treatment at an acid pH (pH 4.0) were simulated in order to study the protective effect of the sorbitol, concentration of gammaglobulin and incubation time, as well as their repercussion on the subsequent pasteurisation step.

Samples of the same batch of IVIG at 5% (Flebogamma, of Instituto Grifols) were taken and a test was carried out to verify the protective effect of the sorbitol during the adjustments of pH in the acid zone, when brought to pH 4.00–4.05 with 0.5 M hydrochloric acid and at an ambient temperature of 20° C.–25° C. Similarly, other tests were also carried out to evaluate the effect of the concentration of gammaglobulin on diluting the starting 5% IVIG with 5% sorbitol solution, as well as the temperature at which adjustment to pH 4.0 was carried out, whether at ambient temperature of 20° C.–25° C. or in the cold at 2° C.–8° C. After incubation at pH 4.0 for 1 hour and subsequent pasteurisation at 60° C.–61° C. for 10 hours in the presence of sorbitol at 33%, the quantification of the aggregates or polymers detectable by O.D. at 280 nm was carried out by means of HPLC. The results obtained are shown in Table 9.

TABLE 9

| | | Adjustment to pH 4.0 at 20° C.–25° C. | | Adjustment to pH 4.0 at 2° C.–8° C. |
|---|---|---|---|---|
| SORBITOL (%) | PROTEIN (%) | Aggregates % (after incubation at pH 4) | Aggregates % (after pasteurising) | Aggregates % (after incubation at pH 4) |
| 5 | 0.25 | N.D. | N.D. | n.d. |
| 5 | 1 | 0.31 | 0.57 | n.d. |
| 5 | 2 | 0.34 | 0.64 | N.D. |
| 5 | 2.5 | N.D. | N.D. | n.d. |
| 5 | 3 | 0.37 | 1.01 | N.D. |
| 5 | 4 | 0.93 | 1.57 | N.D. |
| 5 | 5 | 0.83 | 1.81 | 0.43 |
| 5 | 5 | 0.86 | 3.50 | |
| 10 | 5 | 0.15 | 0.83 | |
| 20 | 5 | 0.10 | N.D. | |
| 33 | 5 | n.d. | 0.70 | | n.d., not detectable
N.D., not determined.
In all cases the starting IVIG did not contain aggregates (n.d.).

The results emphasise the protection exerted by sorbitol when the pH is varied in the acid zone, and even more sharply the higher the temperature. At ambient temperature, a concentration of 10% or more of sorbitol is necessary for efficient protection of gammaglobulin at 5% (or a higher concentration). The concentration of gammaglobulin promotes greater aggregation, notwithstanding the adjustment to pH 4.0 at 2° C.–8° C. concentrations of up to 5% of protein (or more diluted, preferably to 3.5±0.5%) may be reached which would be stabilised with only 5% of sorbitol, and would be acceptable for incubation at an acid pH and subsequent pasteurisation. By adjusting the pH at a temperature of 2° C.–8° C. only a discrete aggregation (0.43% of polymer) was observed at the higher concentration studied of 5% of gammaglobulin with 5% of sorbitol, proving to be significantly lower than when adjusting the pH at 20° C.–25° C. (with 0.83% of polymer). This lower aggregation with the lowering of the temperature, the range of concentration of protein, and also the protection exerted by the sorbitol, justify the conditions established in the various steps of the process of the invention.

The incubation time at an acid pH (pH 4.0 and 36–37° C.) was studied, with regard to the formation of aggregates, with gammaglobulin (Flebogamma) and sorbitol at two different concentrations of both and at a pH adjustment temperature of 2° C.–8° C. The results obtained are to be found in table 10.

TABLE 10

| SORBITOL (%) | PROTEIN (%) | TIME AT pH 4 (hours) | Aggregates % (after treatment at pH 4) | Aggregates % (after pasteurisation) |
|---|---|---|---|---|
| 5 | 2.5 | 1 | n.d. | 0.35 |
| 5 | 2.5 | 2 | 0.30 | 0.59 |
| 5 | 2.5 | 4 | n.d. | 0.32 |
| 6 | 3 | 0 | 0.11 | 0.36 |
| 6 | 3 | 1 | 0.07 | 0.31 |
| 6 | 3 | 4 | 0.07 | 0.41 |
| 6 | 3 | 8 | 0.40 | 1.11 |
| 6 | 3 | 12 | 0.43 | 1.18 |
| 6 | 3 | 24 | 0.15 | 0.58 | n.d., not detectable

The results make quite clear the validity of the two compositions employed for carrying out incubation at an acid pH and subsequent pasteurisation in the presence of sorbitol at 33%. The valid incubation time would be found in the maximum range studied of 0 to 24 hours, with an optional optimum at 4 hours of exposure at 36–37° C.

EXAMPLE 9

The optimum pasteurisation conditions were determined starting from a highly purified 5% IVIG (Flebogamma), directly at 5% concentration (conductivity of about 450 microS/cm) or by dilution 1:1 with water for injection up to 2.5% (conductivity of about 225 microS/cm). To each of the solutions sorbitol was added up to 33% (w/w), adjusting to different pH levels with 0.5 M hydrochloric acid. After subjecting each sample of different concentration and pH to a 10 hour heat treatment at 60° C.–61° C., the molecular distribution was analysed by HPLC to determine the degree of aggregation (polymers or high molecular weight aggregates, and dimers). The values obtained are shown in Table 11.

TABLE 11

| (%) PROTEIN | pH | (%) POLYMERS | (%) DIMERS |
|---|---|---|---|
| 2.5 | 5.52 | 0.46 | 4.36 |
| 2.5 | 5.03 | 0.35 | 3.49 |
| 2.5 | 4.72 | 0.30 | 3.31 |
| 2.5 | 4.51 | 0.45 | 3.34 |
| 5 | 4.2 | 4.89 | 4.54 |
| 5 | 4.0 | 14.42 | 5.60 |
| 5 | 3.8 | 24.51 | 6.23 |

The polymer content in the 5% IVIG used as starting material is undetectable.

The results show that it is feasible to pasteurise at 60° C.–61° C. for 10 hours at a very low ionic strength and at a protein concentration of approximately 2.5%, in a medium stabilised with sorbitol and in a pH range of 5.5 to 4.5, the optimum of which is between pH 4.7 and 5.0, with a minimum increment of aggregates (polymers and dimer).

EXAMPLE 10

Several experiments were carried out to determine the capacity of the method of the invention for eliminating the high molecular weight aggregates arising from (generated by) the previous viral inactivation steps.

The solutions pasteurised in the presence of sorbitol at 33% and subsequently treated with TNBP at 0.3% and polysorbate-80 at 1% of various batches processed in accordance with the method of the invention were diluted with water for injection at a ratio of 1 kg to 1.5 kg of water for every kg of solution, and were then cooled to 2° C.–8° C. Immediately afterwards, PEG-4000 was added to them to bring them to different concentrations and their pH was adjusted to between 7.5 and 8.1. After being left to precipitate the high molecular weight aggregates, the suspensions were filtered through a pore size of 0.5–0.1 micron, a transparent liquid being obtained in each case which contained purified IgG.

The % of polymers was quantified by HPLC of each sample, the values found being shown in Table 12.

TABLE 12

| Process No. | Concentration of PEG (%) | Final pH | Starting solution (% of polymer) | Filtered solution (% of polymer) |
|---|---|---|---|---|
| 61/50 | 3.00 | 7.88 | 2.31 | 0.00 |
| 63/53 | 3.00 | 7.62 | 2.94 | 0.35 |
| 65/58 | 3.15 | 7.51 | 0.88 | 0.33 |
| 63/60 | 3.15 | 8.06 | 2.94 | 0.00 |
| 77/61 | 3.23 | 7.75 | 2.28 | 0.08 |
| 7014/1 | 3.27 | 7.99 | 1.28 | 0.00 |
| 62/59 | 3.45 | 7.47 | 0.84 | 0.00 |

The value not detectable (n.d.) by HPLC has been indicated on this occasion as 0.00.

A total elimination of polymers in the range of PEG concentrations of 3.00% to 3.45% is detected, although there exists an interaction with the pH of the medium, separation proving to be most effective when the pH is between 7.75 and 8.06. At the lowest pH value studied of 7.47, a concentration of at least 3.45% of PEG is required to eliminate the polymer completely, since lower concentrations (for example: PEG 3.15%-pH 7.51) are not able to precipitate said polymers completely and could leave residues in the filtered solution.

The presence of the sorbitol stabiliser likewise works, avoiding the co-precipitation of the non-aggregated species (monomer and dimer) together with the polymer, improving to a great extent the recovery of product in said precipitation. In order to determine the effect of the presence of sorbitol, some tests were carried out on precipitation and recovery of protein (according to optical density) under different concentration conditions. An experiment was carried out starting from a purified 5% IVIG solution (without detectable polymers), this being diluted to an optical density (at 280 nm) of about 6 AU, using water or sorbitol at 10%, depending on the case, and adjusting to pH 8.0. The solution was left to precipitate for at least one hour and then the presence of precipitate was observed. The same experiment was repeated with a solution of IgG coming from the viral inactivation steps of the process of the invention (with a polymer content of 3.97%), being diluted on this occasion with 5% sorbitol or water, and after precipitating and separating the aggregates by filtration, the % of recovery of protein from the filtrate was determined with respect to the initial value.

The results obtained are shown in the following Table 13.

TABLE 13

| CONCENTRATION OF PEG (%) | pH | % POLYMER IN THE STARTING IVIG SOLUTION | CONCENTRATION OF SORBITOL (%) | PRESENCE OF PRECIPITATE (1) | (%) RECOVERY OF PROTEIN IN THE FILTRATE (2) |
|---|---|---|---|---|---|
| 3.0 | 8.0 | n.d. | 0.4 | YES (+++) | N.R. |
| 3.0 | 8.0 | n.d. | 5 | YES (+) | N.R. |
| 3.0 | 8.0 | n.d. | 10 | NO (−) | N.R. |
| 3.0 | 8.0 | 3.97 | 9.4 | YES (+++) | 83.6 |
| 3.0 | 8.0 | 3.97 | 13.0 | YES (+++) | 92.2 |

(1): The number of + signs indicates the amount of precipitate detected:
(+++) abundant;
(+) incipient;
(−) negative.
(2): Percentage of the total protein found in the filtered solution with respect to the initial solution before precipitating.
n.d., not detectable.
N.R., not carried out.

Concentrations of sorbitol above 5% prevent the precipitation of the monomer/dimer of IgG when they are present as single species in the IVIG solution (devoid of polymer), being detected by the absence of precipitate on adding PEG. Similarly, when the polymers contained in the IgG solution are eliminated, an improved recovery of IgG (free of polymers) is observed, at the highest concentration of sorbitol studied (13%). Consequently, the presence of sorbitol during the precipitation of polymers or high molecular weight aggregates is beneficial for preventing co-precipitation and obtaining an optimum recovery of IgG.

EXAMPLE 11

Virus filtration was tested comparatively on a preparatory scale employing commercial filters of nanometric pore size, using for this two different starting materials obtained in accordance with Example 1: solution adjusted to an acid pH (pH=4.00±0.05) at 36±1° C. (material A), and final diafiltered solution at 2.5±0.5% of protein, pH 4.5±0.1 and at 26±1° C. (material B). The results obtained with regard to the amount filtered with respect to the filtration area used, the time taken and the recovery of protein, according to the filters used (Planova 35 N, Planova 15N and DV20) are shown in Table 14.

From the previous table it is clear that both material A and material B are suitable for virus filtration, whether through a pore size of 35 nm or less, up to 15 nm. However, a pore size of around 20 nm appears to be the most suitable, bearing in mind the parameters of recovery of protein (>90%) and productivity (>1 kg/m$^2$) with respect to the virus elimination capacity per pore size of the filter.

What is claimed is:

1. A method for producing virus inactivated human gammaglobulin G, which method comprises:
   (a) suspending a precipitate of human gammaglobulin G in an aqueous solution containing a carbohydrate;
   (b) reducing the content of contaminants in the suspension with PEG;
   (c) applying the suspension to an anionic exchange resin in column to obtain an effluent;
   (d) subjecting the effluent to ultrafiltration so that the content of PEG in said effluent is reduced;
   (e) viral inactivation of the filtered effluent by at least one method selected from the group consisting of (i) Pasteurizing and (ii) treating with solvent/detergent; and
   (f) precipitating and washing the virus inactivated human gammaglobulin G from the viral inactivated effluent.

2. A method for producing virus inactivated human gammaglobulin G according to claim 1, wherein the precipitate of human gammaglobulin G is obtained or provided by fractionation of human plasma with ethanol.

3. A method for producing virus inactivated human gammaglobulin G according to claim 2, wherein the precipitate of human gammaglobulin G comprises fractions II+III of the Cohn method.

4. A method for producing virus inactivated human gammaglobulin G according to claim 1, wherein the carbohydrate is a sugar-alcohol.

5. A method for producing virus inactivated human gammaglobulin G according to claim 4, wherein the sugar-alcohol is sorbitol.

6. A method for producing virus inactivated human gammaglobulin G according to claim 4, wherein the sugar-alcohol is present at a concentration of between 2% and 10% (w/v).

7. A method for producing virus inactivated human gammaglobulin G according to claim 1, in which the step of reducing the concentration of contaminants in the suspension is performed with PEG at a concentration from 2.5% to 5.5% (w/w) and at a pH from 4.8 to 5.5.

8. A method for producing virus inactivated human gammaglobulin G according to claim 1, wherein the pH of the

TABLE 14

| | TYPE OF FILTER | | | | | | | |
|---|---|---|---|---|---|---|---|---|
| | MATERIAL A | | | | MATERIAL B | | | |
| TYPE OF FILTER | Volume Filtered (l/m$^2$) | Protein filtered (kg/m$^2$) | Filtration Time (h) | % Recovery of proteins | Volume filtered (l/m$^2$) | Protein filtered (kg/m$^2$) | Filtration Time (h) | % Recovery of proteins |
| Planova 35N (35 nm) | 213 | 6.77 | 1.53 | 99.2 | 300 | 6.97 | 1.58 | 93.9(*) |
| | | | | | 249 | 5.45 | 3.00 | 96.8 |
| | | | | | 289 | 6.83 | 3.55 | 96.6 |
| DV20 (Pall) (20 nm) | 48.3 | 1.43 | 16.9 | 94.5 | 64.8 | 1.44 | 24 | 93.4 |
| | | | | | 51.7 | 1.14 | 15.9 | 94.8 |
| Planova 15N (15 nm) | 34.0 | 0.99 | 16.2 | 87.1 | 31.0 | 0.59 | 14.9 | 83.1 |
| | | | | | 34.0 | 0.75 | 24.0 | 91.0 |

(*)Recovery obtained prior to post-wash.

suspension is between 5.7 and 6.3 when applied to the anionic exchange resin column.

9. A method for producing virus inactivated human gammaglobulin G according to claim 1, wherein the anionic exchange resin column:
   (a) Contains DEAE-agarose resins, and
   (b) Admits a charge of between 1 g and 2.5 g of fraction II+III per ml of resins.

10. A method for producing virus inactivated human gammaglobulin G according to claim 1, in which the effluent is subjected to ultrafiltration through a membrane of 100 kDa nominal molecular cut-off.

11. A method for producing virus inactivated human gammaglobulin G according to claim 10 in which, after said step of ultrafiltration, the effluent is diafiltered against a solution containing a sugar alcohol.

12. A method for producing virus inactivated human gammaglobulin G according to claim 11, in which the sugar alcohol is sorbitol.

13. A method for producing virus inactivated human gammaglobulin G according to claim 11, in which the sugar alcohol is present in solution at a concentration between 2% and 10% (w/v).

14. A method for producing virus inactivated human gammaglobulin G according to claim 11, in which said diafiltration is performed at a pH between 4.0 and 4.8.

15. A method for producing virus inactivated human gammaglobulin G according to claim 11, in which said diafiltration is performed with a transmembrane pressure below 1.2 bar.

16. A method for producing virus inactivated human gammaglobulin G according to claim 1 further comprising, prior to the step of viral inactivation, a step of treating the filtered effluent at an acid pH.

17. A method for producing virus inactivated human gammaglobulin G according to claim 16, wherein said step of treating the filtered effluent at an acid pH is carried out in the presence of a sugar-alcohol at a pH of 3.95 to 4.05 and at a temperature of 35 to 38° C. from 1 to 4 hours.

18. A method for the production of virus-inactivated human gammaglobulin G according to claim 17 in which the sugar-alcohol is sorbitol, said sorbitol being present at a concentration between 2% and 10% (w/v).

19. A method for the production of virus-inactivated human gammaglobulin G according to claim 1, wherein viral inactivation comprises Pasteurization of the filtered effluent.

20. A method for the production of virus-inactivated human gammaglobulin G according to claim 19 in which the filtered effluent is Pasteurized in the presence of a sugar-alcohol.

21. A method for the production of virus-inactivated human gammaglobulin G according to claim 20, wherein the sugar alcohol is sorbitol.

22. A method for the production of virus-inactivated human gammaglobulin G according to claim 20 in which the sugar alcohol is present at a concentration of between 25% and 35% (w/w).

23. A method for the production of virus-inactivated human gammaglobulin G according to claim 20 in which the filtered effluent is treated with solvent/detergent after said Pasteurization.

24. A method for the production of virus-inactivated human gammaglobulin G according to claim 23 in which, before said treatment with solvent/detergent, the Pasteurized effluent is diluted with water for injection so that:
   (a) the concentration of sugar alcohol is 25% (w/w) or less, and
   (b) the concentration of protein is between 1% and 3% (w/v).

25. A method for the production of virus-inactivated human gammaglobulin G according to claim 1, wherein viral inactivation comprises treatment with solvent/detergent.

26. A method for the production of virus-inactivated human gammaglobulin G according to claim 25 in which, after treatment with said solvent/detergent, the effluent is diluted with water for injection so that the pH is adjusted to between 7.0 and 9.0.

27. A method for the production of virus-inactivated human gammaglobulin G according to claim 26, wherein the pH is adjusted to between 7.8 and 8.4.

28. A method for the production of virus-inactivated human gammaglobulin G according to claim 26 in which the effluent is diluted by adding, for each kilogram of effluent, between 1–2 kg of water for injection.

29. A method for the production of virus-inactivated human gammaglobulin G according to claim 1 in which the virus inactivated human gammaglobulin G is precipitated from the virus inactivated effluent by the addition of PEG.

30. A method for the production of virus-inactivated human gammaglobulin G according to claim 29 in which PEG is added to the virus inactivated effluent to a final concentration between 12% and 17% (w/w).

31. A method for the production of virus-inactivated human gammaglobulin G according to claim 29, in which the precipitated human gammaglobulin G is separated on a tangential flow filtration membrane.

32. A method for the production of virus-inactivated human gammaglobulin G according to claim 31, in which the tangential flow filtration membrane has a pore size from 0.1 to 0.45 microns.

33. A method for the production of virus-inactivated human gammaglobulin G according to claim 31 wherein the precipitate is washed in said tangential flow filtration membrane.

34. A method for the production of virus-inactivated human gammaglobulin G according to claim 33, in which the precipitate is washed by the addition of four or more volumes of solution used to precipitate the virus inactivated human gammaglobulin G.

35. A method for the production of virus-inactivated human gammaglobulin G according to claim 29 wherein the precipitated virus inactivated human gammaglobulin G is solubilized by the addition of an acid solution at pH below 5.5, which acid solution contains a carbohydrate.

36. A method for the production of virus-inactivated human gammaglobulin G according to claim 35 wherein the acid solution comprises acetic acid with an adjusted concentration of between 1 mM to 10 mM.

37. A method for the production of virus-inactivated human gammaglobulin G according to claim 35 wherein the carbohydrate comprises a sugar alcohol.

38. A method for the production of virus-inactivated human gammaglobulin G according to claim 37, in which the sugar alcohol is present at a concentration from 5–20% (w/w).

39. A method for the production of virus-inactivated human gammaglobulin G according to claim 35 wherein said acid solution is adjusted with an alkali to pH 4.0–4.5.

40. A method for the production of virus-inactivated human gammaglobulin G according to claim 35, in which the amount of acid solution added is such that the concentration of PEG in the solubilized human gammaglobulin G is from 2% to 4% (w/w).

41. A method for the production of virus-inactivated human gammaglobulin G according to claim 40, in which the concentration of PEG in the solubilized human gammaglobulin G is from 2.8% to 3.4% (w/w).

42. A method for the production of virus-inactivated human gammaglobulin G according to claim 35, further comprising steps of:
(a) adding an alkali to the acid solution after solubilization of the human gammaglobulin G, so that the pH is adjusted to between 7.5 and 8.5, and
(b) precipitating and separating insoluble high molecular weight aggregates from the pH adjusted solution.

43. A method for the production of virus-inactivated human gammaglobulin G according to claim 42, wherein insoluble high molecular weight aggregates are separated from the pH adjusted solution by filtration.

44. A method for the production of virus-inactivated human gammaglobulin G according to claim 42 further comprising, after separating insoluble high molecular weight aggregates from the pH adjusted solution, diafiltering and concentrating of the solution, pH adjusted to 4.0–4.8, through ultrafiltration membranes of 100 kDa nominal molecular cut-off and at a transmembrane pressure below 1.2 bar.

45. A method for the production of virus-inactivated human gammaglobulin G according to claim 44, wherein the solution is concentrated to a protein concentration of 1% to 3% (w/v) and pH adjusted to 4.4–5.0.

46. A method for the production of virus-inactivated human gammaglobulin G according to claim 44, further comprising steps of:
(a) heating the solution to 25±5° C. after precipitation of insoluble high molecular weight aggregates; and
(b) nanofiltering of the solution through membranes having a nominal pore size of 50 nm or less.

47. A method for producing virus inactivated human gammaglobulin G according to claim 46 wherein the membranes have a nominal pore size of approximately 20 nm.

* * * * *